United States Patent
Zimmerman et al.

(10) Patent No.: US 11,039,939 B2
(45) Date of Patent: Jun. 22, 2021

(54) ORTHOPEDIC TRIAL APPARATUS

(71) Applicant: Smith & Nephew, Inc., Memphis, TN (US)

(72) Inventors: Jacob Ryan Zimmerman, Memphis, TN (US); John Andrew Hall, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 267 days.

(21) Appl. No.: 16/090,629

(22) PCT Filed: Feb. 28, 2017

(86) PCT No.: PCT/US2017/019816
§ 371 (c)(1),
(2) Date: Oct. 2, 2018

(87) PCT Pub. No.: WO2017/151538
PCT Pub. Date: Sep. 8, 2017

(65) Prior Publication Data
US 2019/0117412 A1    Apr. 25, 2019

Related U.S. Application Data

(60) Provisional application No. 62/301,541, filed on Feb. 29, 2016.

(51) Int. Cl.
*A61B 17/58*    (2006.01)
*A61B 17/60*    (2006.01)
(Continued)

(52) U.S. Cl.
CPC ........ *A61F 2/4684* (2013.01); *A61B 17/1668* (2013.01); *A61F 2/3662* (2013.01);
(Continued)

(58) Field of Classification Search
CPC combination set(s) only.
See application file for complete search history.

(56) References Cited

U.S. PATENT DOCUMENTS

| 6,190,416 B1 | 2/2001 | Choteau et al. |
| 9,095,356 B2 | 8/2015 | Thomas et al. |

(Continued)

FOREIGN PATENT DOCUMENTS

| EP | 1437103 A2 | 7/2004 |
| WO | 2007/106752 A2 | 9/2007 |

OTHER PUBLICATIONS

First Office Action for Chinese Patent Application No. 201780014145. 9, dated Mar. 23, 2020.
(Continued)

*Primary Examiner* — Sameh R Boles
(74) *Attorney, Agent, or Firm* — Kacvinsky Daisak Bluni PLLC

(57) ABSTRACT

An orthopedic trial apparatus (100) including an orthopedic component (110) having a distal shaft portion (112) positionable within a passage in a bone and a proximal shaft portion (114) extending from the distal shaft portion, and a proximal trial assembly (120) engaged with the proximal shaft portion of the orthopedic component. The proximal trial assembly includes a proximal spacer (130) component and a proximal trial component (150). The proximal spacer component is rotationally engaged with the proximal shaft portion of the orthopedic component to substantially prevent relative rotation therebetween about a longitudinal axis. The proximal trial component is axially coupled to the proximal spacer component to prevent disengagement of the proximal trial component from the proximal spacer component while (Continued)

permitting selective rotation of the proximal trial component relative to the proximal spacer component about the longitudinal axis.

21 Claims, 11 Drawing Sheets

(51) Int. Cl.
    *A61F 2/00*     (2006.01)
    *A61F 2/46*     (2006.01)
    *A61F 2/36*     (2006.01)
    *A61B 17/16*     (2006.01)
    *A61F 2/30*     (2006.01)

(52) U.S. Cl.
    CPC ............... *A61F 2002/3054* (2013.01); *A61F 2002/30367* (2013.01); *A61F 2002/30494* (2013.01); *A61F 2002/30505* (2013.01); *A61F 2002/30507* (2013.01); *A61F 2002/30538* (2013.01); *A61F 2002/30601* (2013.01); *A61F 2002/30777* (2013.01); *A61F 2002/3652* (2013.01)

(56) References Cited

U.S. PATENT DOCUMENTS

| | | |
|---|---|---|
| 9,439,785 B2 | 9/2016 | Huddle et al. |
| 2004/0054419 A1 | 3/2004 | Serra et al. |
| 2004/0122440 A1 | 6/2004 | Daniels et al. |
| 2004/0267267 A1* | 12/2004 | Daniels ................ A61F 2/3662 606/80 |
| 2012/0259338 A1 | 10/2012 | Carr et al. |
| 2013/0325019 A1 | 12/2013 | Thomas et al. |

OTHER PUBLICATIONS

International Search Report and Written Opinion for International Application No. PCT/US2017/019816 dated Jun. 22, 2017.
International Preliminary Report on Patentability for International Application No. PCT/US2017/019816 dated Sep. 4, 2018.
Notice of reason for rejection for Japanese Application No. 2018-544306, dated Jan. 18, 2021, original and translated document, 4 pages.
Office Action for Chinese patent application No. 201780014145.9 dated Mar. 2, 2021, original and translated document, 16 pages.

* cited by examiner

ORTHOPEDIC TRIAL APPARATUS

CROSS-REFERENCE TO RELATED APPLICATIONS

This application is a United States National Phase filing of International Application No. PCT/US2017/019816, filed on Feb. 28, 2017, which claims the benefit of U.S. Provisional Application No. 62/301,541 filed Feb. 29, 2016, the contents of which are incorporated herein by reference in their entirety.

FIELD OF THE INVENTION

The present invention generally relates to an orthopedic trial apparatus, and more particularly, but not exclusively, relates to an apparatus for preparing bone and trialing the bone for receipt of a prosthetic device in an orthopedic procedure.

BACKGROUND

Some modular orthopedic systems include distal stem trials, proximal sleeve trials, proximal body segment trials, and proximal trial necks that replicate a prosthetic implant. An implant may be selected based on the trial instrumentation to provide the best fit for the patient. Using distal stem trials adds to the number of instruments in the system, which in turn tends to increase inventory overhead and associated manufacturing costs. A greater number of instruments and devices may also lead to confusion in the operating room (OR), and may contribute to a larger cleanup/sterilization operation and a corresponding increase in costs. As such, there have been efforts to simplify instrumentation in such a way that surgeons or surgical assistants are not burdened by handling large, heavy instrument sets including multiple instruments and devices.

In conventional orthopedic surgical systems, a surgeon removes a reamer system from a femoral canal and replaces each sequential reamer with a distal stem trial interconnected with a proximal trial. Each time a reamer is removed and a distal stem trial is inserted in its place, there are risks of fracture and/or excessive bone removal since the distal stem trial adds an additional scratch-fit step. In cases of poor bone quality, these risks may be substantially increased. In addition to an increased risk of fracture associated with each reamer removal step, there is also an increase in OR time for the surgeon. The OR time required to ream the femoral canal, remove the reamer from the femoral canal, and implant a distal stem trial can result in significant surgery time and associated costs.

Some orthopedic surgical systems are described in commonly-owned U.S. Pat. No. 8,690,875, the contents of which are incorporated herein by reference in their entirety. Such systems utilize a distal reamer that serves multiple purposes. More particularly, the reamer is first used to distally ream the femoral canal, and is left in place within the canal. The reamer is configured to allow a modular proximal trial and trial neck assembly to be connected to the reamer in such a way that trial reduction may be performed immediately after termination of a cutting operation by the reamer. As a result, the modular trial and trial neck segments allow quick trial reduction with the reamer maintained within the femoral canal. Moreover, by trialing off of the reamer, the system avoids the need for a separate set of stem trials.

The standard practice for implanting a hip system is to prepare the bone using a first set of instruments, and then perform a trial reduction using a second set of instruments different from the first set. Conventionally, reamers clear a passage within a femoral canal, and then a trial stem is selected from a kit and inserted into the formed passage. Trial reduction takes place using the trial stem. After the joint is reduced, the trial stem is removed from the femoral canal and is subsequently replaced with a correspondingly-sized implant stem. This standard practice generally takes more time to perform, and is somewhat inefficient because more instruments, devices and method steps are needed to carry out the procedure. Additionally, more time spent in the operating room results in the patient's incremental exposure to increased risk, and also increases hospital overhead and associated costs.

Despite some advancement within the surgical field, many apparatuses for preparing bone for prosthetic devices often encounter problems during the trialing step. In particular, it can be difficult to assemble the proximal trial spacer component and the trial neck body assembly onto the reamer shaft. Additionally, it can be unclear to the surgeon whether or not the spacer component is fully seated on the reamer shaft due to limitations or restrictions on visualization of the spacer component and the reamer, and it can also be difficult to align the body component with the reamer shaft so that adjacent threads are properly engaged with one another. This can be particularly problematic when soft tissue is positioned laterally adjacent the body, with the soft tissue exerting a medial or lateral force onto the spacer and body components and potentially forcing the components out of alignment with one another and/or with the reamer during the assembly process. Also, when the components need to be disassembled, it is often difficult to remove the spacer component without special tools, particularly in cases where the spacer component is short or of a smaller size. In addition, when assembled to the reamer, the spacer component is positioned within the femoral canal, and is therefore not easily accessible by the surgeon. Not only do these problems result in a lengthened surgical procedure, but can also lead to surgeon frustration.

The present invention addresses these concerns and provides other benefits and advantages in a novel and unobvious manner.

SUMMARY

While the actual nature of the invention covered herein can only be determined with reference to the claims appended hereto, certain forms of the invention that are characteristic of the embodiments disclosed herein are described briefly as follows.

It is one object of the invention to provide an improved orthopedic trial apparatus, particularly, but not exclusively, for trialing a bone for receipt of a prosthetic device as part of an orthopedic surgical procedure. Further embodiments, forms, features, aspects, benefits, objects, and advantages of the present invention will become apparent from the detailed description and figures provided herewith.

In one form of the invention, an orthopedic trial apparatus is provided which includes an orthopedic component and a proximal trial assembly. The orthopedic component has a distal shaft portion configured for positioning within a passage in a bone, and a proximal shaft portion extending from the distal shaft portion. The proximal trial assembly is engaged with the proximal shaft portion of the orthopedic component, and includes a proximal spacer component and a proximal trial component. The proximal spacer component is rotationally engaged with the proximal shaft portion of the orthopedic component to substantially prevent relative rotation therebetween about a longitudinal axis, and the proximal trial component is axially coupled to the proximal spacer component to prevent disengagement of the proximal trial component from the proximal spacer component while permitting selective rotation of the proximal trial component relative to the proximal spacer component about the longitudinal axis.

In another form of the invention, an orthopedic trial apparatus is provided which includes an orthopedic component and a proximal trial assembly. The orthopedic component has a distal shaft portion configured for positioning within a passage in a bone, and a proximal shaft portion extending from the distal shaft portion. The proximal trial assembly is engaged with the proximal shaft portion of the orthopedic component, and includes a proximal spacer component and a proximal trial component. The proximal spacer component is rotationally engaged with the proximal shaft portion of the orthopedic component to substantially prevent relative rotation therebetween about a longitudinal axis, and the proximal trial component is axially aligned with and coupled to the proximal spacer component to prevent axial misalignment and disengagement of the proximal trial component from the proximal spacer component while permitting selective displacement of the proximal trial component relative to the proximal spacer component along the longitudinal axis and selective rotation of the proximal trial component relative to the proximal spacer component about the longitudinal axis.

In a further form of the invention, an orthopedic trial apparatus is provided which includes an orthopedic component and a proximal trial assembly. The orthopedic component has a distal shaft portion configured for positioning within a passage in a bone, and a proximal shaft portion extending from the distal shaft portion. The proximal trial assembly is engaged with the proximal shaft portion of the orthopedic component, and includes a proximal spacer component and a proximal trial component. The proximal spacer component is telescopically engaged with the proximal spacer component to permit selective axial movement therebetween and to maintain axial alignment of the proximal trial component relative to the proximal spacer component generally along the longitudinal axis while permitting selective rotation of the proximal trial component relative to the proximal spacer component about the longitudinal axis. The proximal trial component is axially biased away from the proximal spacer component by a biasing element, and the proximal trial component and the proximal spacer component define anti-rotation elements that are positioned in selective engagement by a locking member to selectively prevent rotation of the proximal trial component relative to the proximal spacer component about the longitudinal axis.

DESCRIPTION OF THE ILLUSTRATED EMBODIMENTS

Figure 1:
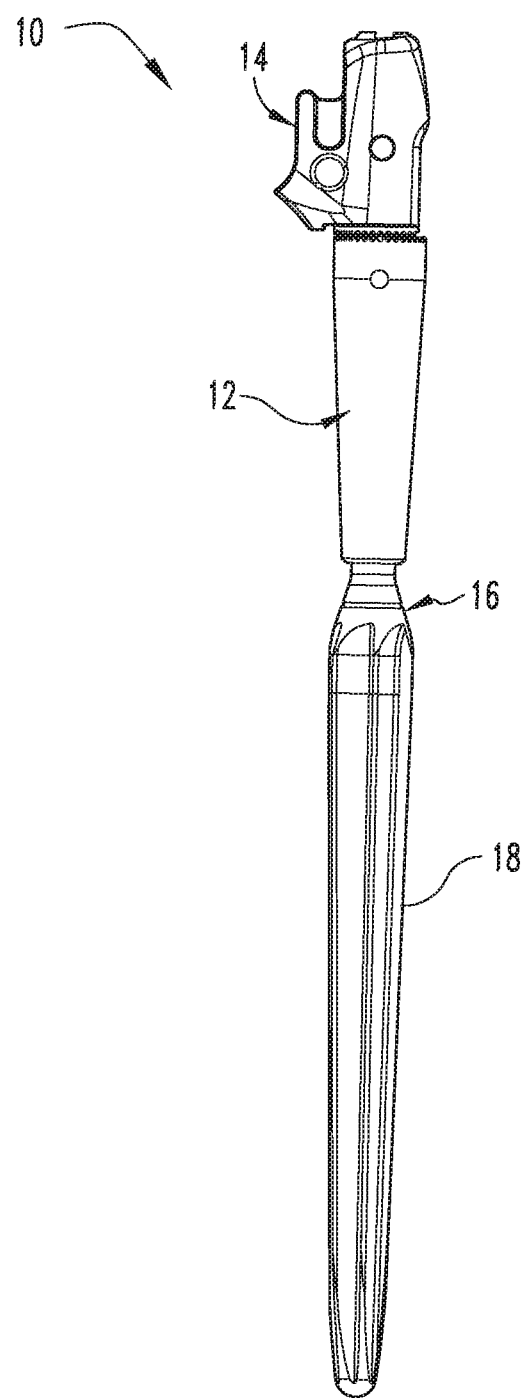
FIG. 1 is an assembled view of a conventional orthopedic trialing system.

For the purpose of promoting an understanding of the principles of the present invention, reference will now be made to the embodiments illustrated in the drawings and specific language will be used to describe the same. It will nevertheless be understood that no limitation of the scope of the invention is hereby intended. Any alterations and further modifications in the described embodiments, and any further applications of the principles of the invention as described herein are contemplated as would normally occur to one skilled in the art to which the invention relates.

The following descriptions and illustrations of non-limiting embodiments of the invention are exemplary in nature, it being understood that the descriptions and illustrations related thereto are not intended to limit or restrict the inventions disclosed herein and/or their applications and/or uses.

Figure 2:
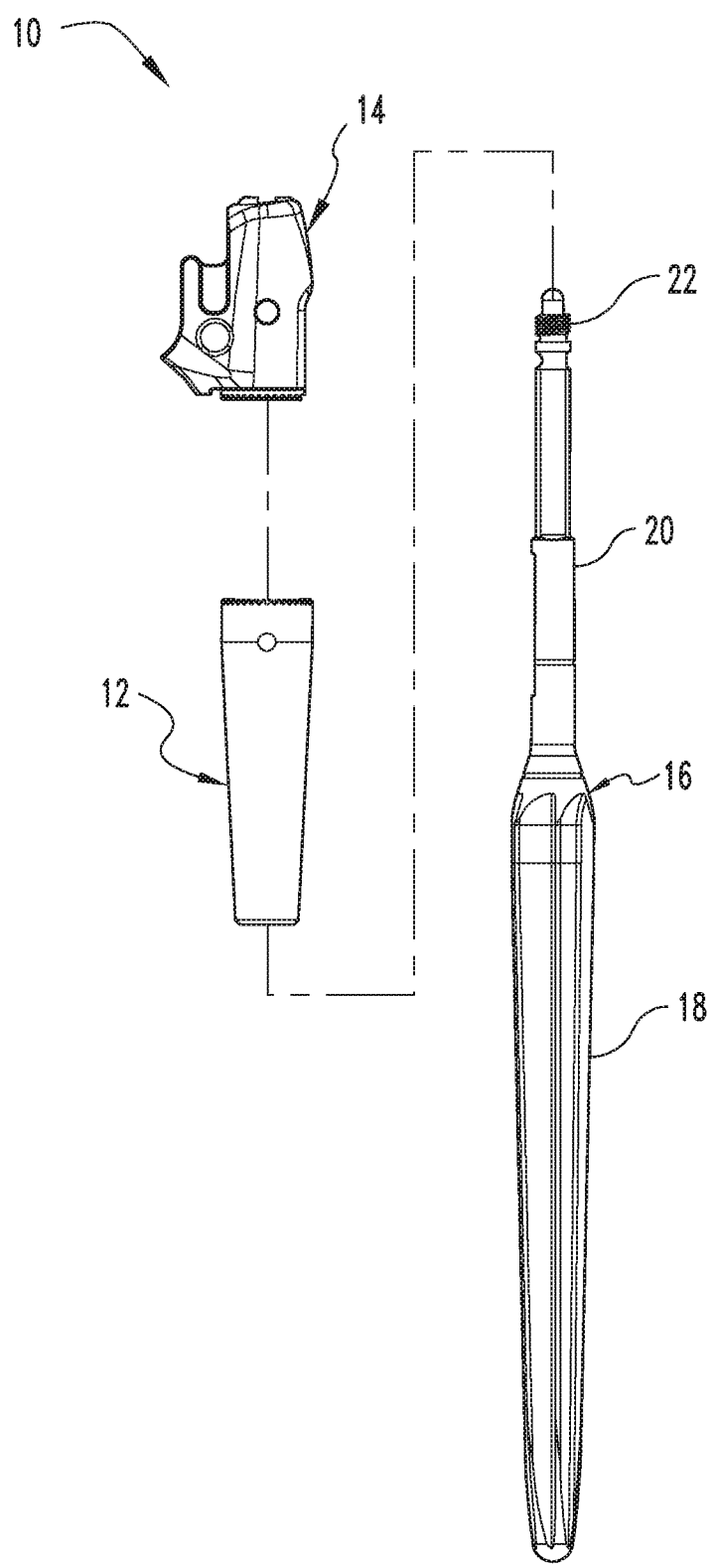
FIG. 2 is an exploded view of the orthopedic trialing system of FIG. 1.

FIGS. 1 and 2 respectively illustrate assembled and exploded views of a conventional orthopedic trialing system 10. The trialing system 10 generally includes a proximal trial spacer component 12 and a proximal trial neck body component 14, with each component operatively engaged with a reamer 16 having a distal cutting portion 18 and proximal shaft portion 20. The trial spacer component 12 is primarily used to support and position the trial neck body component 14 on the proximal shaft portion 20 of the reamer 16.

In the illustrated embodiment, the trial spacer component 12 and the trial neck body component 14 are provided as separate and independent components of the trialing system 10 that are separable from one another, as shown most clearly in FIG. 2. It should be appreciated that the trial spacer component 12 and the trial neck body component 14 are not positively engaged or otherwise interconnected with one another to prevent separation and misalignment of these components.

With regard to the trialing system 10, it can be difficult to determine whether the trial spacer component 12 is fully seated on the proximal shaft portion 20 of the reamer 16 because of restricted or limited visibility of the trial spacer component 12 relative to the proximal shaft portion 20 due to the presence of surrounding tissue and other anatomic structures. It can also be difficult to accurately align the trial neck body component 14 with a threaded stem 22 of the proximal shaft portion 20 to ensure proper threaded engagement with a locking component (not shown), particularly when soft tissue abuts against the trial neck body component 14 and forces the trial neck body component 14 out of axial alignment with the proximal shaft portion 20. Furthermore, disassembly of the trialing system 10 can be difficult without the use of special tools, and due to limited visibility and/or access to the trial spacer component 12 and/or the trial neck body component 14 when positioned within the femoral canal and surrounded by soft tissue.

Figure 3:
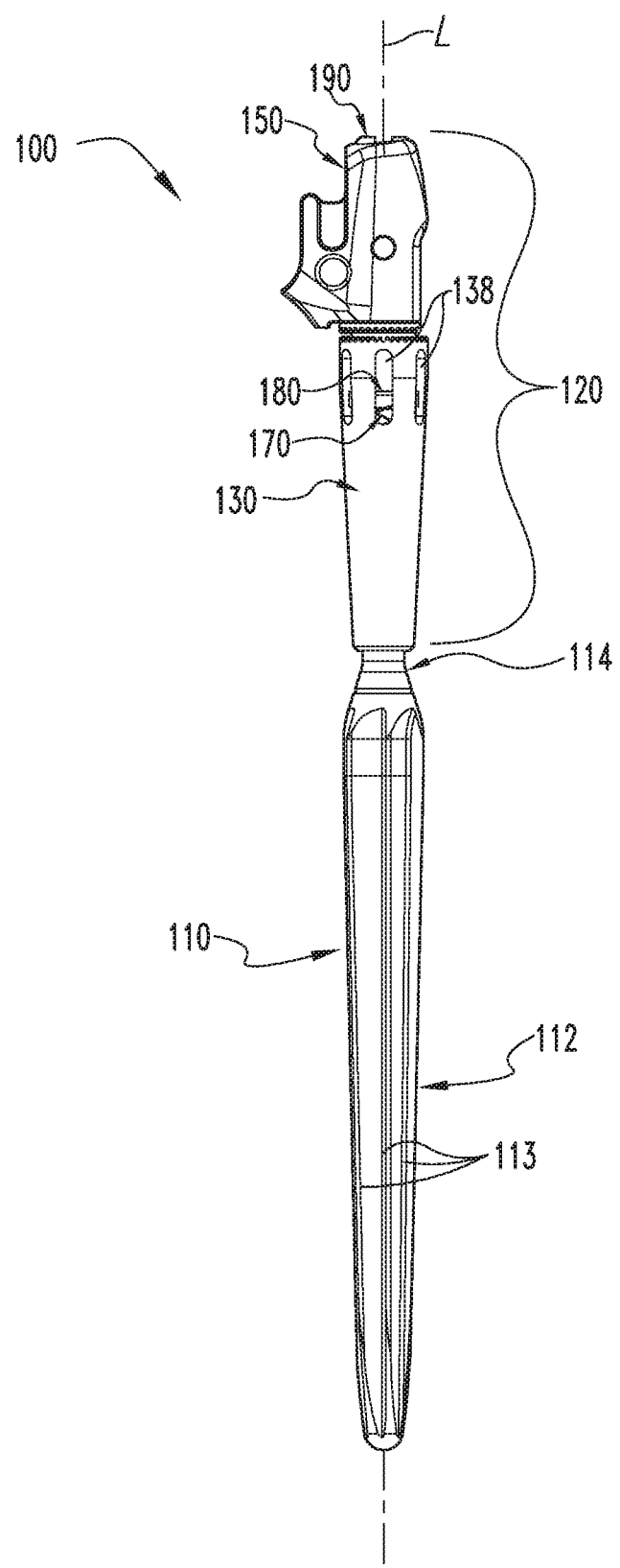
FIG. 3 is an assembled view of an orthopedic trial apparatus according to one form of the invention.
Figure 4:
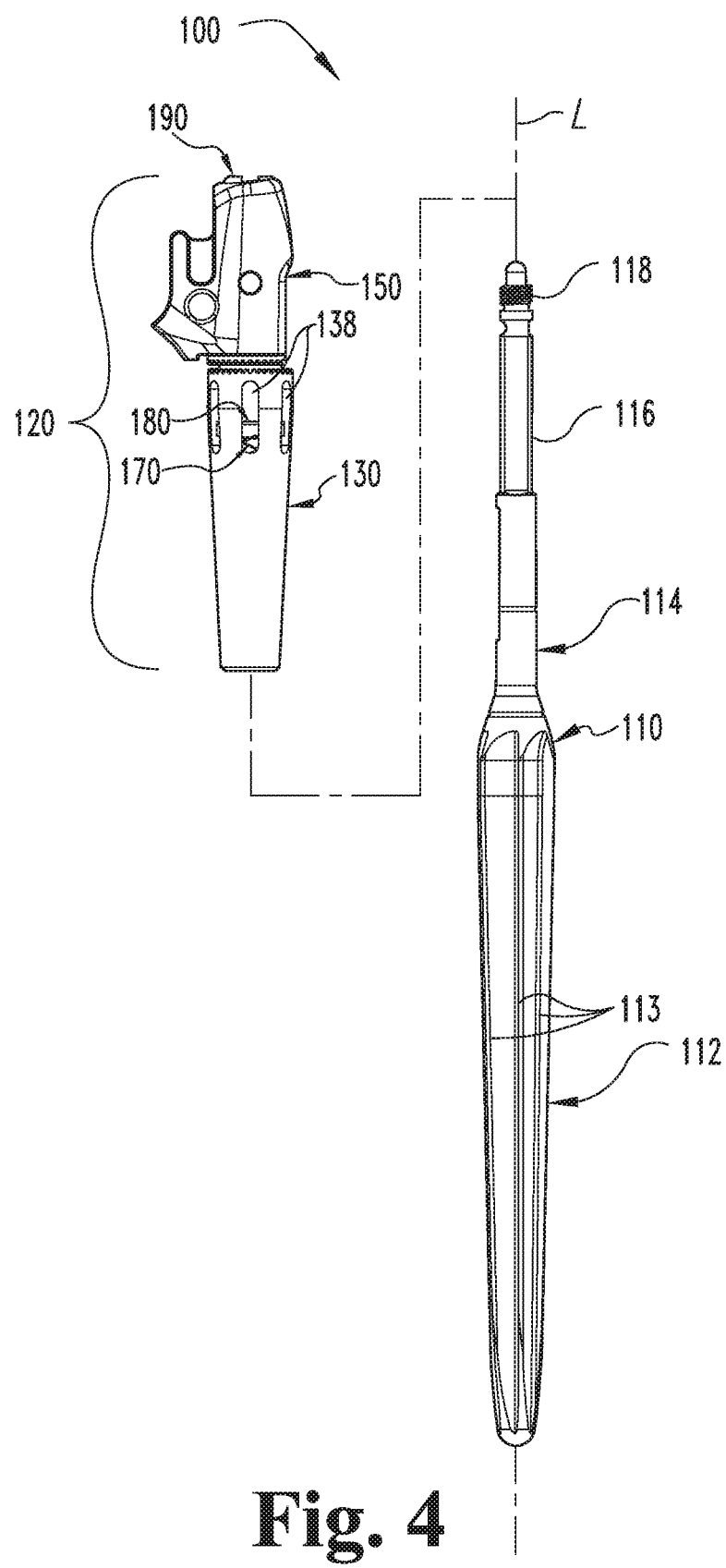
FIG. 4 is an exploded view of the orthopedic trial apparatus of FIG. 3.
Figure 5:
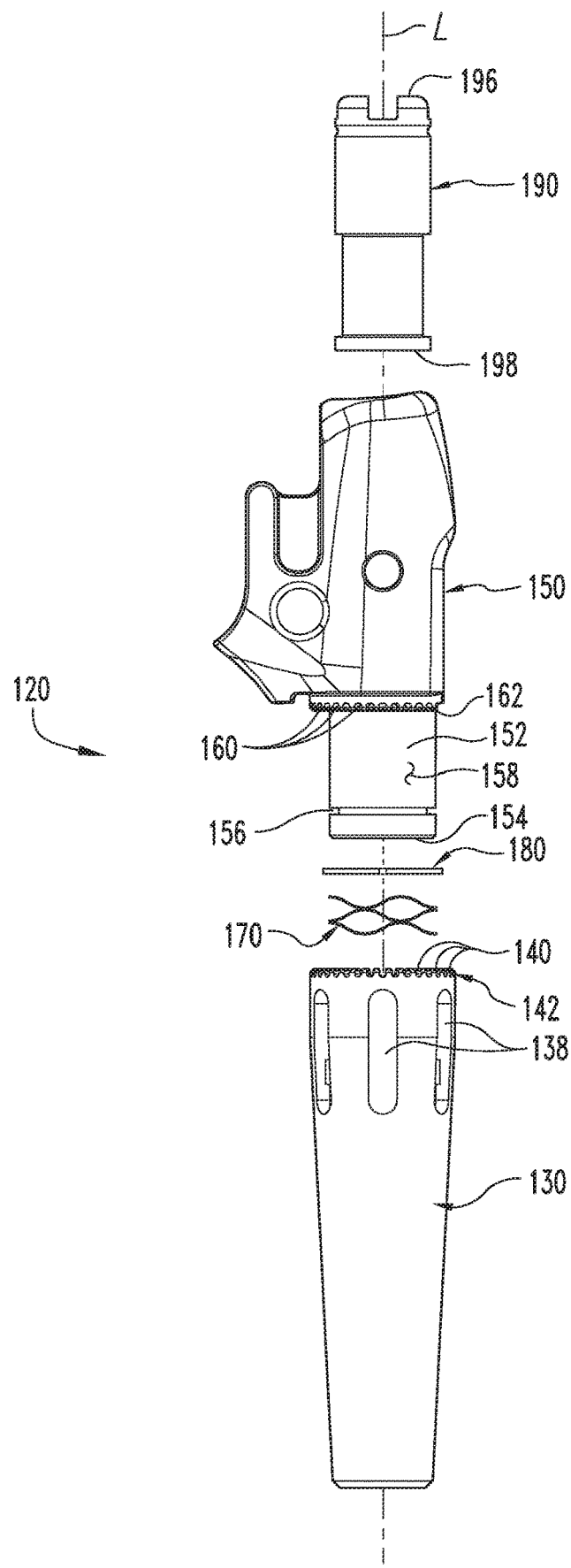
FIG. 5 is an exploded view of a trial and spacer assembly for use with the orthopedic trial apparatus of FIG. 3.
Figure 6:
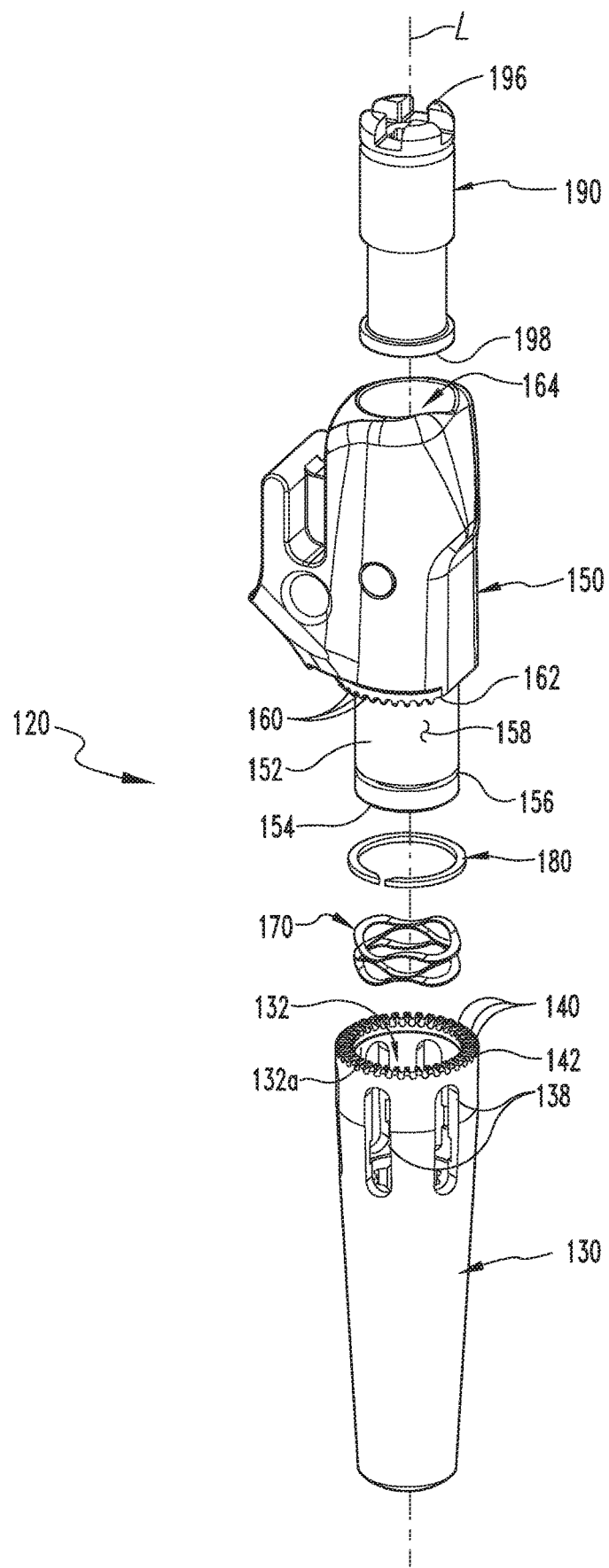
FIG. 6 is an exploded perspective view of the trial and spacer assembly of FIG. 5.
Figure 7:
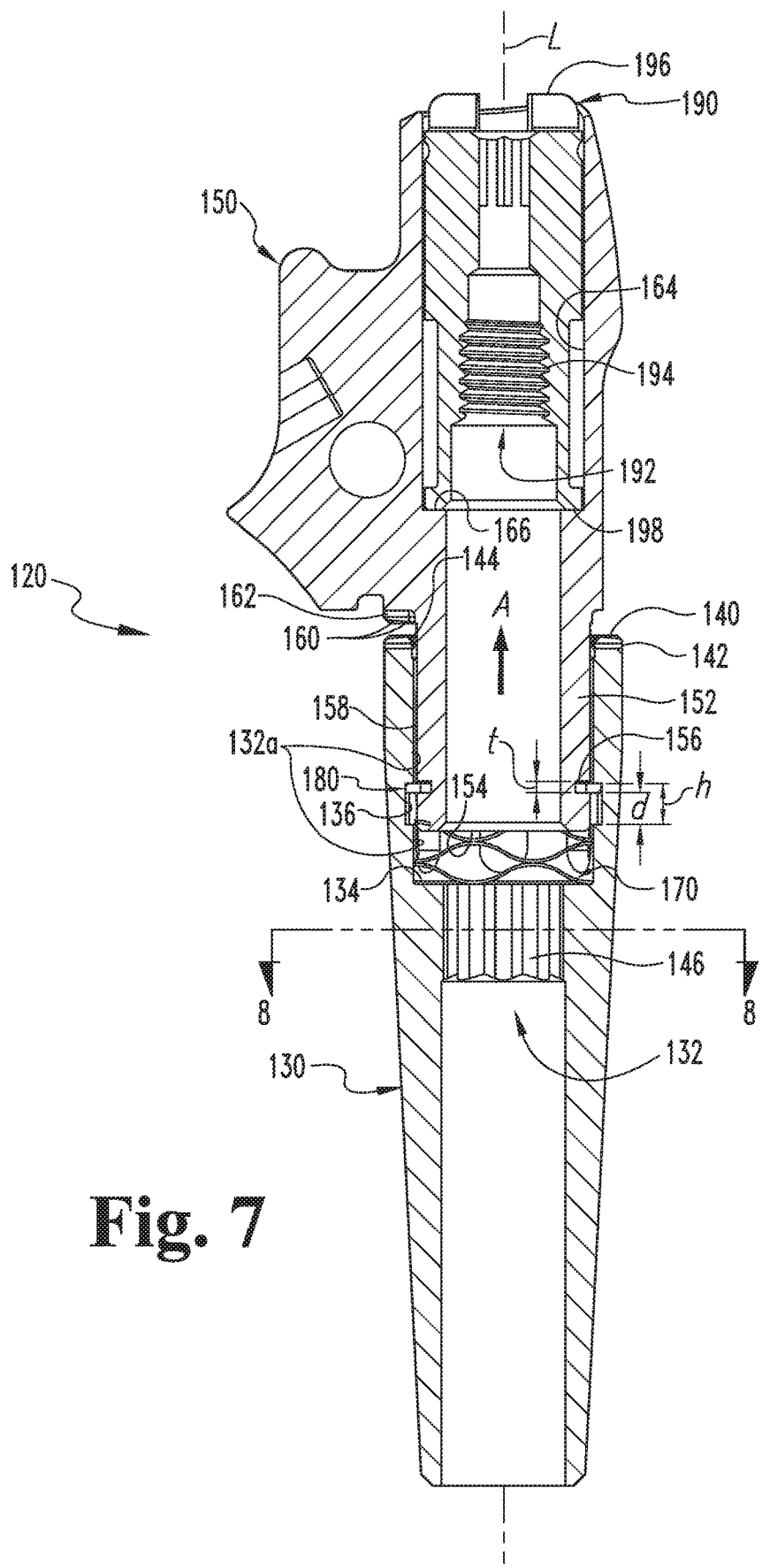
FIG. 7 is an assembled cross-sectional view of the trial and spacer assembly of FIG. 5.

With reference to FIGS. 3 and 4, illustrated therein is an orthopedic trial apparatus 100 according to one form of the present invention. The trial apparatus 100 generally includes an orthopedic component 110 and a proximal trial assembly 120. In one embodiment, the proximal trial assembly 120 is selectively and removably engaged with the orthopedic component 110 to provide the assembled trial apparatus 100 for use as a trial instrument in association with a bone, including long bones such as, for example, the femur. However, in other embodiments, the proximal trial assembly 120 may be permanently and non-removably engaged with the orthopedic component 110.

The orthopedic component 110 has a distal shaft portion 112 configured for positioning within a passage in a bone, and a proximal shaft portion 114 extending from the distal shaft portion 112. In one embodiment, the orthopedic component 110 is configured as a cutting instrument, and the distal shaft portion 112 is configured as a cutting portion including one or more cutting elements 113 adapted to cut bone and at least partially form the passage in the bone. In one particular embodiment, the cutting instrument 110 is configured as a reamer a having a number of cutting flutes 113 extending along the length of a distal cutting portion 112. However, it should be appreciated that other types and configurations of cutting instruments are also contemplated including, for example, a drill or any other instrument configured to cut bone. In another embodiment, the orthopedic component 110 may be configured as an orthopedic implant, with the distal shaft portion 112 configured as an elongate stem positionable within a passage in the bone, such as the intramedullary canal of a long bone including the femur. In one particular embodiment, the orthopedic implant 110 may be configured as a hip prosthesis, with the elongate stem 112 configured as a modular stem portion structured for engagement with a modular head portion of the orthopedic implant.

The proximal trial assembly 120 is engaged with the proximal shaft portion 114 of the orthopedic component 110, and generally includes a proximal spacer component 130 and a proximal trial component 150. The proximal spacer component 130 is rotationally engaged with the proximal shaft portion 114 of the orthopedic component 110 to substantially prevent relative rotation therebetween about a longitudinal axis L. The trial component 150 is axially coupled to the spacer component 130 to prevent disengagement of the trial component 150 from the spacer component 130, while permitting selective rotation of the trial component 150 relative to the spacer component 130 about the longitudinal axis L. Further aspects of the proximal trial assembly 120, including the interconnection and engagement of the spacer component 130 with the trial component 150, will be discussed in greater detail below.

Referring collectively to FIGS. 1-7, in one embodiment, the trial component 150 is selectively movable relative to the spacer component 130 in a direction generally along the longitudinal axis L, and the trial component 150 is maintained in axial alignment with the spacer component 130 generally along the longitudinal axis L. Although the trial component 150 is illustrated as having a particular shape and configuration, it should be appreciated that the trial component 150 can be provided with other shapes and configurations suitable for use in association with the trial apparatus 100.

In the illustrated embodiment, the trial component 150 is axially biased away from the spacer component 130 by at least one biasing element 170 such as, for example, a spring. The biasing element 170 is positioned within an axial passage 132 in the spacer component 130 and abuts against an interior shoulder or shelf 134 formed by a counter bore region 132a of the axial passage 132, and also abuts against an opposing end surface 154 of the trial component 150 to thereby axially bias the trial component 150 in a direction away from the spacer component 130 (indicated by arrow A in FIG. 7). In one embodiment, the biasing element 170 is configured as a wave spring. However, other types of springs and other configurations of biasing elements 170 are also contemplated for use in association with the invention including, for example, a coil spring, a leaf spring, or any other structure suitable to axially bias the trial component 150 away from the spacer component 130. It should also be understood that the trial apparatus 100 need not necessarily include a biasing element 170. Instead, the trial component 150 may be manually pulled away from the spacer component 130.

Additionally, in the illustrated embodiment, the trial component 150 is telescopically engaged with the spacer component 130 to permit selective axial movement therebetween and to maintain axial alignment of the trial component 150 relative to the spacer component 130 generally along the longitudinal axis L. Specifically, the trial component 150 includes a lower stem portion 152 positioned within the counter bore region 132a of the axial passage 132 in the spacer component 130 to provide telescopic engagement therebetween to permit selective axial movement between the trial component 150 and the spacer component 130 along the longitudinal axis L, and to substantially maintain the trial component 150 in axial alignment with the spacer component 130 generally along the longitudinal axis L due, at least in part, to a relatively close-fitting engagement of the stem portion 152 with the inner wall of the counter bore region 132a of the axial passage 132. It should be appreciated that in other embodiments of the invention, the spacer component 130 may define a stem portion positioned within a counter bore region or axial passage in the trial component 150 to provide telescopic engagement therebetween. It should also be appreciated that other suitable interconnections between the trial component 150 and the spacer component 130 are also contemplated to permit selective axial movement therebetween and to maintain axial alignment of the trial component 150 relative to the spacer component 130.

Further, in the illustrated embodiment, the trial apparatus 100 includes structural elements and features that prevent disengagement of the trial component 150 from the spacer component 130, while permitting the trial component 150 to rotate relative to the spacer component 130 (and relative to the orthopedic component 110 which is rotationally coupled to the spacer component 130). In one embodiment, a lateral projection 180 defined by one of the trial component 150 and the spacer component 130 is axially displaced along an axially-extending groove to permit axial displacement of the trial component 150 relative to the spacer component 130, while preventing disengagement of the trial component 150 from the spacer component 130. In this manner, the trial component 150 and the spacer component are positively engaged with one another to prevent separation, but are still permitted to rotate and axially translate relative to one another about/along the longitudinal axis L.

In the illustrated embodiment, the lateral projection is defined by a retaining ring 180 positioned within an annular groove 156 defined in an outer surface 158 of the stem portion 152 of the trial component 150, and the axially-extending groove is defined by an undercut 136 in the counter bore region 132a of the axial passage 132 in the spacer component 130. The undercut region 136 defines an annular groove having a groove height h that is significantly greater than a thickness t of the retaining ring 180 to thereby allow a limited amount of axial translation or displacement d of the trial component 150 relative to the spacer component 130 (i.e., d=t−h). In other embodiments, the retaining ring 180 may be associated with the spacer component 130, and the axially-extending groove 136 may be associated with the trial component 150 (i.e., a reversal of the lateral projection and the axially-extending groove). It should be appreciated that other suitable interconnections between the trial component 150 and the spacer component 130 are also contemplated to prevent axial disengagement between the trial component 150 and the spacer component 130, including the embodiment associated with the trial apparatus 200 illustrated in FIGS. 9-11 and discussed in further detail below. In another embodiment, instead of using a retaining ring 180 to maintain axial engagement of the trial component 150 with the spacer component 130, the stem portion 152 of the trial body 150 may be provided with a plurality of axially-extending slots or slits extending from the end of the stem portion 152 to form a number of flexible segments. A bump could be formed on an end portion of each flexible segment for sliding engagement within a corresponding axially-extending groove formed along the counter bore region 132a of the axial passage 132 to maintain axial engagement of the trial component 150 with the spacer component 130. Additionally, a reverse configuration is also contemplated.

In one embodiment of the invention, the retaining ring 180 is provided as a snap ring, and is assembled with the trial component 150 by radially expanding the snap ring 180, positioning the snap ring 180 about the stem portion 152 adjacent the annular groove 156, and releasing the snap ring 180 into position within the annular groove 156. The depth of the annular groove 156 is sized such that when the stem portion 152 is inserted into the counter bore region 132a of the axial passage 132, the snap ring 180 is permitted to collapse or contract within the annular groove 156 to allow the stem portion 152 to be fully inserted into the counter bore region 132a. When the snap ring 180 reaches the axially-extending groove 136 in the spacer component 130, the snap ring 180 outwardly expands into the axially-extending groove 136, thereby positively locking or engaging the trial component 150 into axial engagement with the spacer component 130, while still permitting the trial component 150 to freely rotate and axially translate relative to the spacer component 130 about/along the longitudinal axis L. A chamfer 144 (FIG. 7) may be provided on the leading end or edge of the axial passage 132 in the spacer component 130 which acts as a ramp to facilitate collapsing of the snap ring 180 into the annular groove 156 of the stem portion 152 during initial insertion into the axial passage 132 of the spacer component 130.

As also shown in the illustrated embodiment, the spacer component 130 may be provided with a number of openings or windows 138 extending through the wall of the spacer component 130 and located along the counter bore region 132a of the axial passage 132 that receives the biasing element 170, the retaining ring 180, and the lower end of the stem portion 152 of the trial component 150 to provide visualization of the interior components and/or to facilitate cleaning and sterilization of the interior components. In the illustrated embodiment, the windows 138 are configured as a plurality of axially extending slots positioned uniformly about the perimeter of the spacer component 130. However, other shapes, sizes and configurations of the windows 138 are also contemplated.

In the illustrated embodiment, the trial component 150 and the spacer component 130 define anti-rotation features that are positioned in selective engagement with one another to selectively prevent rotation of the trial component 150 relative to the spacer component 130 about the longitudinal axis L. In one embodiment, the trial component 150 defines a number of radially-extending splines or teeth 160 formed on an axially-facing shoulder 162 that are positioned in selective, intermeshing engagement with a number of radially-extending splines or teeth 140 formed on an opposing end 142 of the spacer component 130 to selectively prevent rotation of the trial component 150 relative to the spacer component 130 about the longitudinal axis L.

In a further embodiment, once the trialing process associated with the trial component 150 is complete (i.e., the trial component is moved to the desired position/orientation relative to the orthopedic component 110, and its position/orientation is selected relative to adjacent structures and anatomic features), the anti-rotation elements or radially-extending splines 140, 160 are selectively engaged with one another by a compression or locking mechanism 190 to selectively prevent rotation of the trial component 150 relative to the spacer component 130, thereby locking the trial component 150 in a selected rotational and axial position relative to the spacer component 130 and the orthopedic component 110.

In the illustrated embodiment, the compression or locking mechanism 190 is configured as an end cap or nut defining a passage 192 (FIG. 7) and including an internally threaded region 194 that is threadingly engaged with an externally threaded end region 118 (FIG. 4) of the proximal shaft portion 114 of the orthopedic component 110. The end cap 190 includes a shaped proximal end 196 that defines features which facilitate rotation of the end cap 190 with a driver instrument. In the illustrated embodiment, the shaped proximal end 196 defines crossing slits to facilitate rotation of the end cap 190 by a flat blade driver. However, other suitable shapes and configurations of the end cap 190 and the shaped proximal end 196 are also contemplated. The end cap 190 is positioned within an axial passage 164 extending through the trial component 150, with the threaded end region 118 of the proximal shaft portion 114 of the orthopedic component 110 positioned within the passage 192 of the end cap 190, and an end surface or shoulder 198 of the end cap 190 positioned in abutment against an inner shoulder or ledge 166 defined within the axial passage 164 of the trial component 150. As should be appreciated, rotation of the end cap 190 exerts a compression force onto the trial component 150 via compressing abutment of the end surface 198 against the inner shoulder 166, which displaces the trial component 150 toward and into engagement with the spacer component 130, which in turn compresses the radially-splined surfaces 140, 160 into intermeshing engagement with one another. Compression of the radially-splined surfaces 140, 160 into intermeshing engagement with one another selectively prevents further rotational or axial movement of the trial component 150 relative to the spacer component 130 and the orthopedic component 110, thereby locking the trial component 150 in a selected position and orientation relative to the orthopedic component 110.

Figure 8:
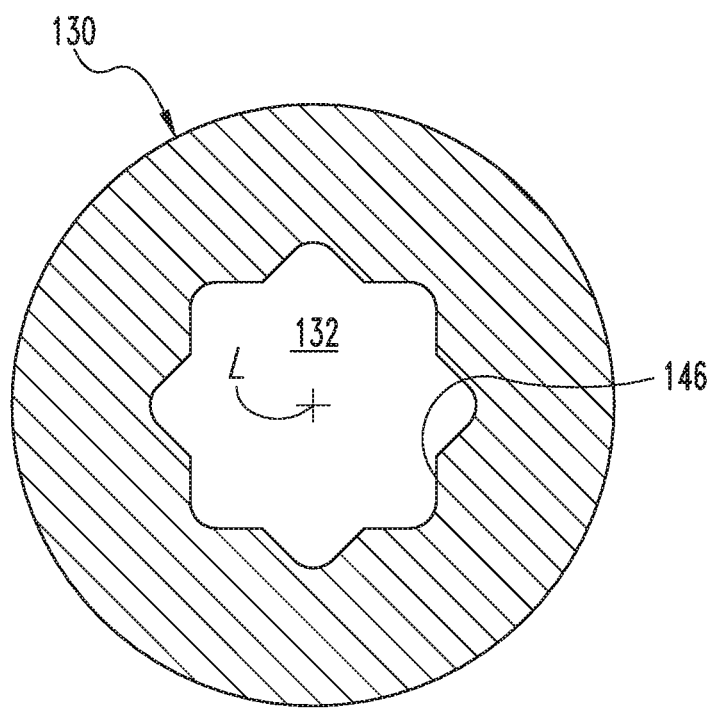
FIG. 8 is a cross-sectional view through a central opening in the spacer component taken along line 8-8 of FIG. 7.

Referring to FIG. 8, in the illustrated embodiment, the spacer component 130 of the trial assembly 120 is keyed to the proximal shaft portion 114 of the orthopedic component 110 to substantially prevent relative rotation therebetween about the longitudinal axis L. Specifically, a region of the axial passage 132 extending through the spacer component 130 defines a non-circular inner cross section 146 (FIGS. 7 and 8), and a corresponding region of the proximal shaft portion 114 defines a non-circular outer cross section 116 (FIG. 4) that is rotationally engaged with the non-circular inner cross section 146 to substantially prevent relative rotation between the spacer component 130 and the proximal shaft portion 114 of the orthopedic component 110.

In one embodiment, the non-circular inner cross section 146 has a double square pattern defined by two square-shaped inner cross sections that are angularly offset from one another by 45 degrees, and the non-circular outer cross section 116 is generally square-shaped. However, it should be understood and appreciated that other shapes and configurations of the non-circular outer cross section 116 and/or the non-circular inner cross section 146 are also contemplated including, for example, a single square inner cross section, a rectangular cross-section, an oblong cross section, a hexagonal cross section, a splined cross section, a Torx-shaped cross section, a star-shaped cross section, or any other suitable keyed configuration to rotationally couple the trial spacer 130 with the proximal shaft portion 114 of the orthopedic component 110 to substantially prevent relative rotation therebetween about the longitudinal axis L.

As should be appreciated, although the spacer component 130 and the trial component 150 constitute individual pieces, these components are axially coupled, interconnected, or combined with one another to form a single, integrated trial assembly 120, with the spacer component 130 and the trial component 150 being rotationally independent from one another (i.e., the components are free to rotate relative to one another). Additionally, the spacer component 130 and the trial component 150 are axially locked into position atop the proximal shaft portion 114 of the orthopedic component 110 such that the integrated trial assembly 120 functionally operates as if the spacer component 130 and the trial component 150 were provided as separate and independent components, as shown in the conventional embodiment illustrated in FIGS. 1 and 2.

As should be further appreciated, having the spacer component 130 and the trial component 150 combined into a single, integrated unit simplifies connection or engagement of the trial assembly 120 with the orthopedic component 110. The spacer component 130 is operatively engaged with and axially coupled to the trial component 150 in such a manner as to minimize difficulties in determining when the spacer component 130 is fully seated on the proximal shaft portion 114 of the orthopedic component 110. Further, the trial component 150 is maintained in axial alignment with the spacer component 130 such that the internally threaded region 194 of the locking cap 190 cannot easily be pushed out of alignment with the externally threaded end region 118 of the orthopedic component 110 during final assembly of the trial apparatus 100, thereby minimizing the risk of mis-threading or cross-threading. Additionally, compared to traditional/conventional trial systems, the components of the trial assembly 120 (i.e., the trial component 150 and the spacer component 130) are significantly easier to disassemble from the orthopedic component 110, particularly since the integrated trial assembly 120 may be removed as a single unit rather than having to individually remove the trial component 150, and then separately removing the spacer component 130 from the bone passage or canal in view of the visual obstructions caused by soft tissue or other surrounding anatomic structures.

Figure 9:
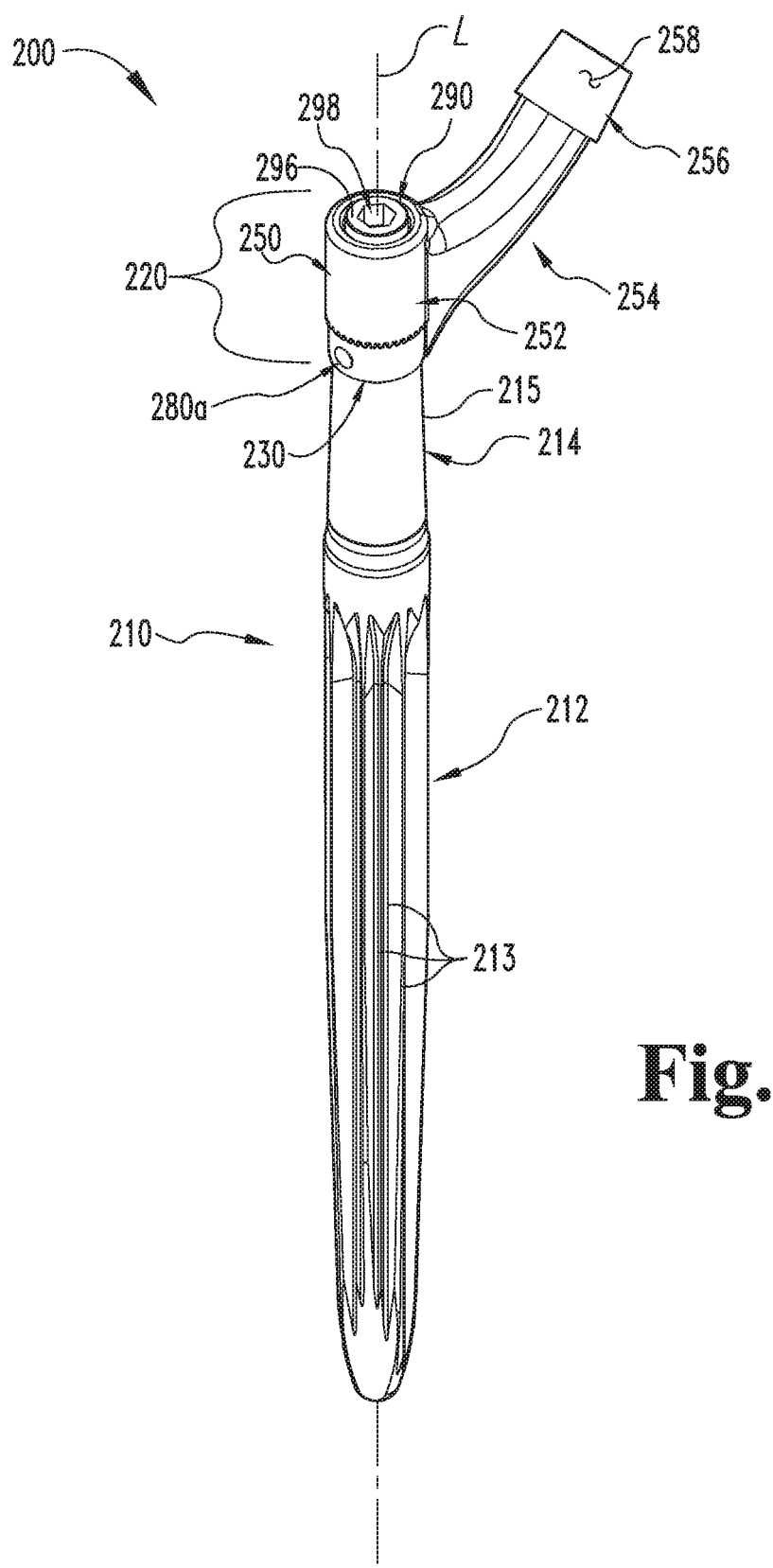
FIG. 9 is an assembled view of an orthopedic trial apparatus according to another form of the invention.
Figure 10:
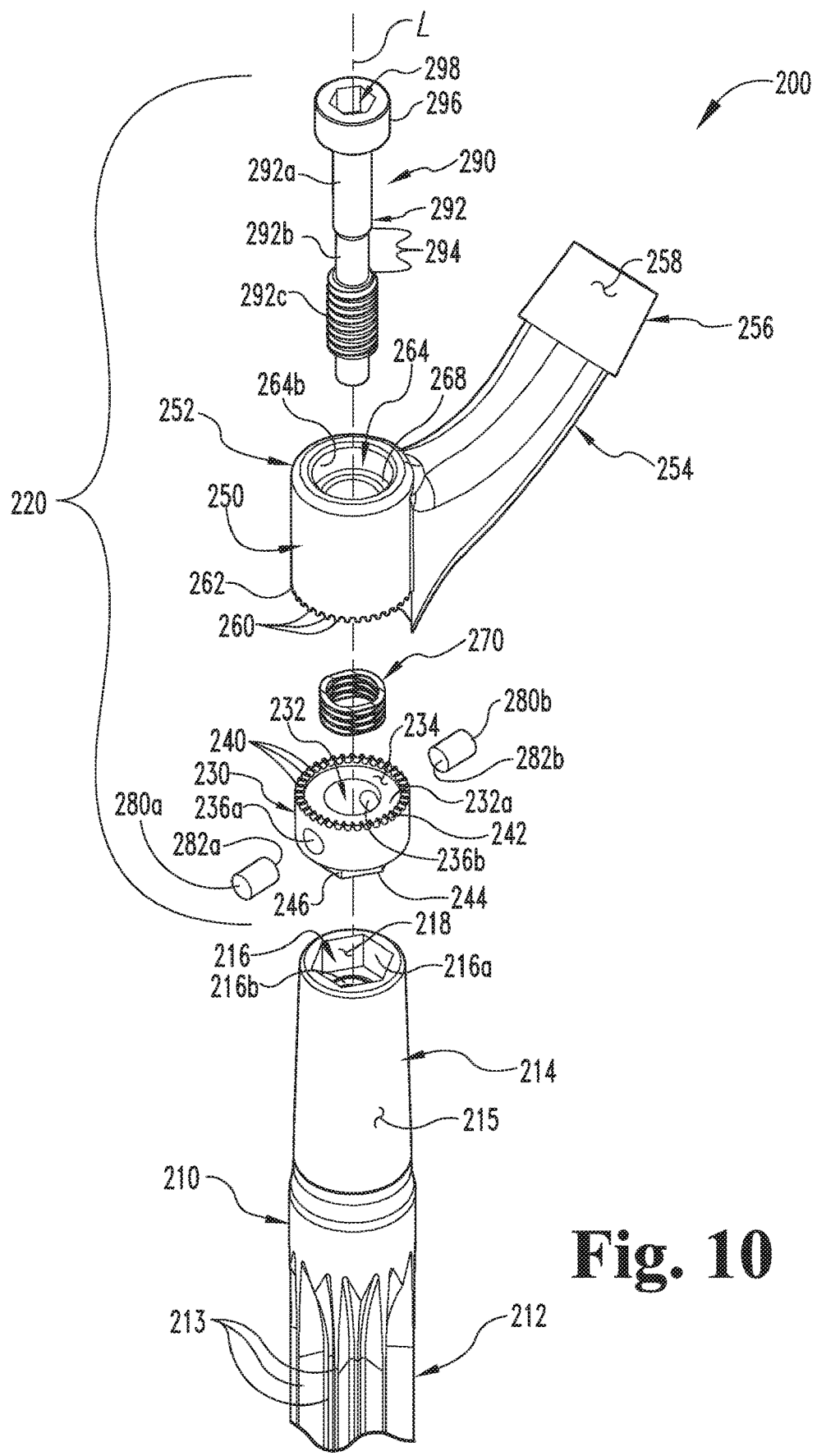
FIG. 10 is an exploded view of the orthopedic trial apparatus of FIG. 9.
Figure 11:
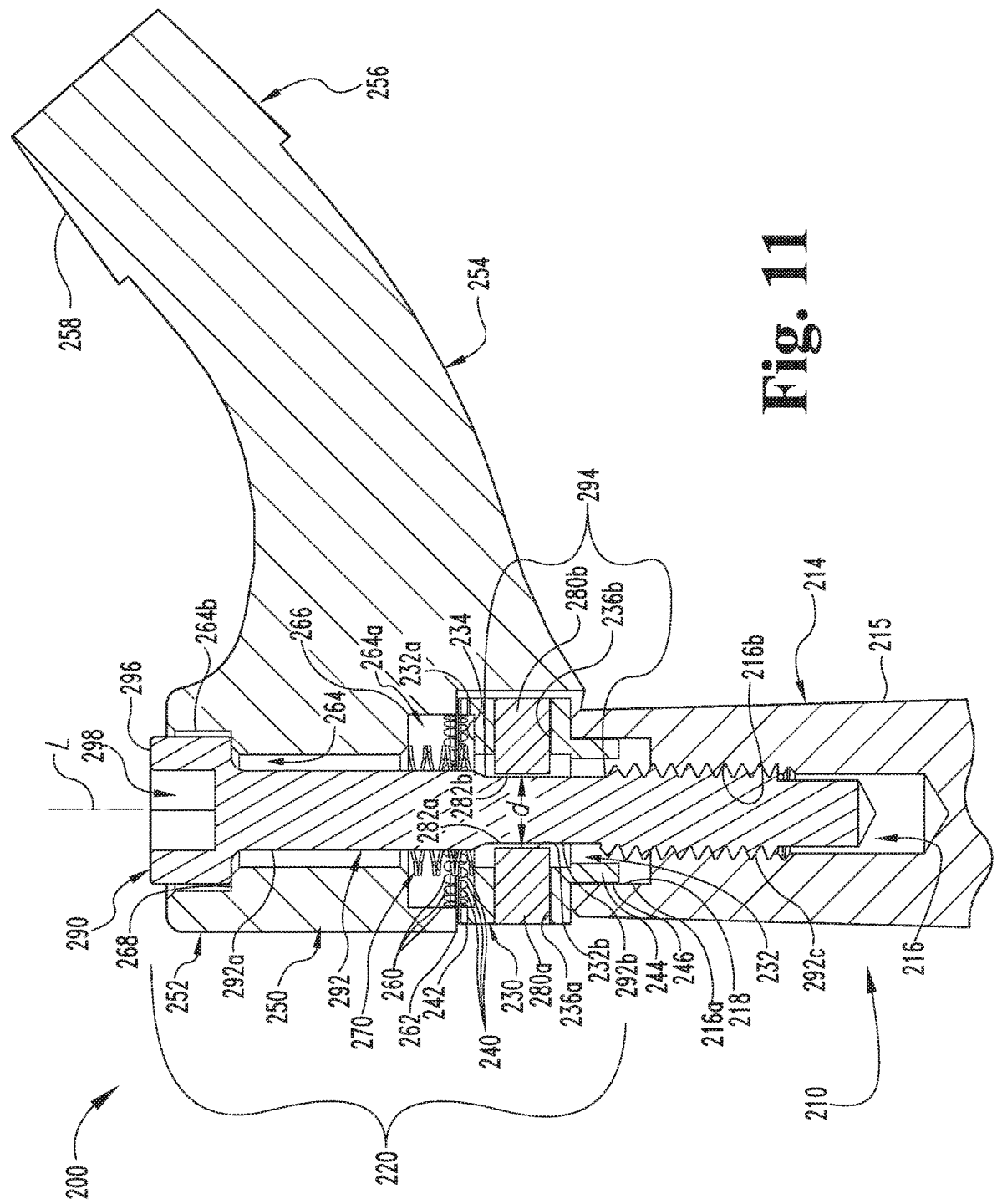
FIG. 11 is an assembled cross-sectional view of the trial and spacer assembly for use with the orthopedic trial apparatus of FIG. 9.

Referring collectively to FIGS. 9-11, illustrated therein is an orthopedic trial apparatus 200 according to another form of the present invention. The orthopedic trial apparatus 200 has operational characteristics and features that are generally similar to those of the orthopedic trial apparatus 100 illustrated in FIGS. 1-8 and described in detail above. However, some of the related components have structural and functional differences, the likes of which will be discussed below. The trial apparatus 200 generally includes an orthopedic component 210 and a proximal trial assembly 220. In one embodiment, the proximal trial assembly 220 is selectively and removably engaged with the orthopedic component 210 to provide the assembled trial apparatus 200 for use as a trial instrument in association with a bone, including long bones such as, for example, the femur. However, in other embodiments, the proximal trial assembly 220 may be permanently and non-removably engaged with the orthopedic component 210.

The orthopedic component 210 has a distal shaft portion 212 configured for positioning within a passage in a bone, and a proximal shaft portion 214 extending from the distal shaft portion 212. In one embodiment, the orthopedic component 210 is configured as an orthopedic implant, with the distal shaft portion 212 configured as an elongate stem positionable within a passage in the bone, such as the intramedullary canal of a long bone including the femur.

In one specific embodiment, the orthopedic component 210 is configured as a modular hip prosthesis, with the elongate stem 212 configured as a modular stem portion positionable within the intramedullary canal of the femur, and which is structured for engagement with a proximal implant portion (not shown) of the hip prosthesis. The distal shaft portion 212 includes a plurality of engagement or anchoring elements 213 adapted to engage the inner walls of the bone passage to anchor the orthopedic component 210 within the bone. In the illustrated embodiment, the anchoring elements 213 extend along a substantial length of the distal shaft portion 212 and are configured as elongate fins positioned about the perimeter of the distal shaft portion 212. Additionally, in the illustrated embodiment, the proximal shaft portion 214 defines a tapered outer surface 215 that outwardly tapers along the longitudinal axis L in a proximal-to-distal direction. The tapered outer surface 215 is configured to mate with a tapered opening in the proximal implant portion (not shown) which is assembled with the orthopedic component 210 subsequent to removal of the proximal trial assembly 220 upon completion of the trialing process. Notably, the trial apparatus 200 is configured such that the proximal trial assembly 220 does not engage or contact the tapered outer surface 215, which avoids potential marring or damage to the tapered outer surface 215 that might otherwise negatively affect final assembly/engagement of the proximal implant portion with the orthopedic component 210. It should be appreciated that assembly of the proximal trial assembly 220 with the orthopedic component 210 without engagement or contact with the tapered outer surface 215 provides an advantage over other trial apparatuses or devices which allow for engagement/contact of the trial assembly with the orthopedic component. Although a particular configuration of the orthopedic component 210 has been illustrated and described herein, it should be appreciated that other types and configurations of orthopedic components, implants, devices or instruments are also contemplated for use in association with the present invention.

The proximal trial assembly 220 is engaged with the proximal shaft portion 214 of the orthopedic component 210, and generally includes a proximal spacer component 230 and a proximal trial component 250. The proximal spacer component 230 is rotationally engaged with the proximal shaft portion 214 of the orthopedic component 210 to substantially prevent relative rotation therebetween about a longitudinal axis L. The trial component 250 is axially coupled to the spacer component 230 to prevent disengagement of the trial component 250 from the spacer component 230, while permitting selective rotation of the trial component 250 relative to the spacer component 230 about the longitudinal axis L. Further aspects of the proximal trial assembly 220, including the interconnection and engagement of the spacer component 230 with the trial component 250, will be discussed in greater detail below.

Similar to the trial component 150 and the spacer component 130 of the trial apparatus 100, the trial component 250 is selectively movable relative to the spacer component 230 in a direction generally along the longitudinal axis L, and the trial component 250 is maintained in axial alignment with the spacer component 230 generally along the longitudinal axis L. In the illustrated embodiment, the trial component 250 includes a cylindrical-shaped body portion 252, a neck portion 254 extending laterally from the body portion 252, and a head engagement portion 256 configured for engagement with a modular trial head (not shown). In one embodiment, the head engagement portion 256 defines a tapered outer surface 258 to facilitate secure engagement between the trial component 250 and the modular trial head. Although the trial component 250 is illustrated as having a particular shape and configuration, it should be appreciated that the trial component 250 can be provided with other shapes and configurations suitable for use in association with the trial apparatus 200.

Additionally, similar to the trial component 150 illustrated and described above with regard to the trial apparatus 100, the trial component 250 is axially biased away from the spacer component 230 by at least one biasing element 270 such as, for example, a spring. The biasing element 270 is partially positioned within an axial recess or counter bore region 232a formed along an axial passage 232 extending through the spacer component 230, and abuts against a shelf or shoulder 234 formed by a bottom surface of the counter bore region 232a. The biasing element 270 is also partially positioned within an axial recess or counter bore region 264a formed along an axial passage 264 extending through the body portion 252 of the trial component 250, and abuts against a shelf or shoulder 266 formed by a bottom surface of the counter bore region 264a. The biasing element 270 also extends about a shaft portion 292a of a threaded fastener 290 to maintain the biasing element 270 in proper alignment with the trial component 250 and the spacer component 230. In one embodiment the locking element 290 is configured as a threaded fastener such as, for example, a bolt. Further features of the locking element 290 will be described in detail below. It should be understood that other types and configurations of the locking element 290 are also contemplated.

Abutment of the biasing element 270 between the shoulders 234, 266 defined by the spacer component 230 and the trial component 250, respectively, serves to axially bias the trial component 250 in a direction away from the spacer component 230. In one embodiment, the biasing element 270 is configured as a wave spring. However, other types of springs and other configurations of biasing elements 270 are also contemplated for use in association with the invention including, for example, a coil spring, a leaf spring, or any other structure suitable to axially bias the trial component 250 away from the spacer component 230. It should also be understood that the trial apparatus 200 need not necessarily include a biasing element 270. Instead, the trial component 250 may be manually pulled away from the spacer component 230.

Additionally, in the illustrated embodiment, the trial component 250 is telescopically engaged or coupled with the spacer component 230 to permit selective axial movement therebetween, and to maintain axial alignment of the trial component 250 relative to the spacer component 230 generally along the longitudinal axis L. Specifically, the trial component 250 includes a shaft or stem 292 (defined by the locking element 290) including a reduced cross sectional portion 292b that is positioned within a reduced cross sectional portion 232b of the axial passage 232 extending through the spacer component 230 to provide telescopic engagement therebetween to permit selective axial movement between the trial component 250 and the spacer component 230 along the longitudinal axis L, and to aid in substantially maintaining the trial component 250 in axial alignment with the spacer component 230 generally along the longitudinal axis L due, at least in part, to a relatively close-fitting engagement of the reduced cross sectional portion 292b of the stem 292 with the inner wall(s) of the reduced cross sectional portion 232b of the axial passage 232. It should be appreciated that in other embodiments of the invention, the spacer component 230 may define a stem portion including a region positioned within a corresponding region of the axial passage 264 in the trial component 250 to provide telescopic engagement therebetween. It should also be appreciated that other suitable interconnections between the trial component 250 and the spacer component 230 are contemplated to permit selective axial movement therebetween, and to maintain axial alignment of the trial component 250 relative to the spacer component 230.

Further, in the illustrated embodiment, the trial apparatus 200 includes structural elements and features that prevent disengagement of the trial component 250 from the spacer component 230, while permitting the trial component 250 to rotate relative to the spacer component 230 (and relative to the orthopedic component 210 which is rotationally coupled to the spacer component 230). In one embodiment, one or more lateral projections defined by one of the trial component 250 and the spacer component 230 is axially displaced along an axially-extending groove to permit axial displacement of the trial component 250 relative to the spacer component 230, while preventing disengagement of the trial component 250 from the spacer component 230. In this manner, the trial component 250 and the spacer component are positively engaged with one another to prevent separation, but are still permitted to rotate and axially translate relative to one another about/along the longitudinal axis L.

In the illustrated embodiment, the lateral projection(s) is/are defined by a pair of pins or guides 280a, 280b that are positioned in corresponding openings 236a, 236b extending laterally through the side wall of the spacer component 230 and into communication with the axial passage 232 extending through the spacer component. The pins 280a, 280b extend into the axial passage 232 and define opposing end surface or faces 282a, 282b, respectively that together define the reduced cross sectional portion 232b of the axial passage 232. The opposing end surfaces 282a, 282b are separated from one another by a distance d that closely corresponds to the outer diameter of the reduced cross section shaft portion 292b of the threaded fastener 290 (FIG. 11). As should be appreciated, the pins 280a, 280b are permitted to axially translate along a length of the reduced cross sectional portion 232b of the axial passage 232, but cannot translate axially beyond the reduced cross sectional portion 232b of the axial passage 232 due to the increased cross section defined by the first shaft portion 292a and the externally threaded shaft portion 292c of the threaded fastener 290 (i.e., the first shaft portion 292a and the externally threaded shaft portion 292c each define an outer diameter that is greater than the distance d separating the opposing end surfaces 282a, 282b of the pins 280a, 280b). As a result, the spacer component 230 is captured on the threaded fastener 290 via the pins 280a, 280b. Additionally, the threaded fastener 290 also extends though the axial passage 264 in the trial component 250, thereby maintaining the trial component 250 in axial engagement with the spacer component 230. The increased cross sectional profiles defined by the first shaft portion 292a and the externally threaded shaft portion 292c of the threaded fastener 290 effectively define an axially-extending groove 294 along which the pins 280a, 280b are permitted to axially translate to permit a degree of axial translation of the spacer component 230 relative to the trial component 250, while still maintaining axial engagement between the spacer component 230 and trial component 250.

In one embodiment, the trial component 250, the spacer component 230, and the threaded fastener 290 may be assembled using the following procedure. With the pins 280a, 280b initially disassembled from the spacer component 230, the shaft portion 292 of the threaded fastener 290 is inserted through the axial passage 264 in the trial component 250, and through the axial passage 232 in the spacer component 230. With the lateral openings 236a, 236b positioned adjacent the reduced cross section shaft portion 292b of the threaded fastener 290, the pins 280a, 280b are inserted into the lateral openings 236a, 236b and are secured within the lateral openings 236a, 236b by a suitable process, such as, for example, deformation, welding, fastening, or by any other suitable means for securing. With the pins 280a, 280b secured to the spacer component 230 and positioned within the axially-extending groove 294 defined along the shaft portion 292b of the threaded fastener 290, the trial component 250 is thereby positively locked or interconnected in axial engagement with the spacer component 230, while still permitting the trial component 250 to freely rotate and axially translate relative to the spacer component 230 about/along the longitudinal axis L.

Although the illustrated embodiment of the spacer component 230 is provided with the pins 280a, 280b, it should be understood that the pins 280a, 280b may alternatively be associated with the trial component 250, and the axially-extending groove may alternatively be associated with the spacer component 230 (i.e., a reversal of the lateral projections and the axially-extending groove). Additionally, although the illustrated embodiment includes a pair of pins 280a, 280b, it should be appreciated that any number of pins could be used, including a single pin or three or more pins. It should also be appreciated that other suitable interconnections between the trial component 250 and the spacer component 230 are also contemplated to prevent axial disengagement between the trial component 250 and the spacer component 230, including the embodiment associated with the trial apparatus 100 illustrated in FIGS. 1-8 and discussed in detail above.

In the illustrated embodiment, the trial component 250 and the spacer component 230 define anti-rotation features that are positioned in selective engagement with one another to selectively prevent rotation of the trial component 250 relative to the spacer component 230 about the longitudinal axis L. In one embodiment, the trial component 250 defines a number of radially-extending splines or teeth 260 formed on an axially-facing end surface 262 that are positioned in selective, intermeshing engagement with a number of radially-extending splines or teeth 240 formed on an opposing axially-facing end surface 242 of the spacer component 230 to selectively prevent rotation of the trial component 250 relative to the spacer component 230 about the longitudinal axis L.

In a further embodiment, once the trialing process associated with the trial component 250 is complete (i.e., the trial component is moved to the desired position/orientation relative to the orthopedic component 210, and its position/orientation is selected relative to adjacent structures and anatomic features), the anti-rotation elements or radially-extending splines 240, 260 are selectively engaged with one another by a compression or locking mechanism 290 to selectively prevent rotation of the trial component 250 relative to the spacer component 230, thereby locking the trial component 250 in a selected rotational and axial position relative to the spacer component 230 and the orthopedic component 210.

In the illustrated embodiment, the compression or locking mechanism 290 is structured as a threaded fastener or bolt defining a shaft 292 including a first shaft portion 292a extending through the axial passage 264 in the trial component 250, a second shaft portion 292b extending through the axial passage 232 in the spacer component 230, an externally threaded shaft portion 292c that is threadingly engaged with an internally threaded portion 216b of an axial passage 216 in the proximal shaft portion 214 of the orthopedic component 210, and a head portion 296 positioned within a counter bore region 264b of the axial passage 264 extending through the trial component 250. The threaded fastener 290 includes a shaped proximal recess 298 which facilitates rotation of the threaded fastener 290 with a driver instrument (not shown). In the illustrated embodiment, the shaped proximal recess 298 has a hexagonal shape to facilitate rotation of the threaded fastener 290 by a driver instrument having a hexagonal-shaped end portion. However, it should be understood that other suitable shapes and configurations of the threaded fastener 290 and the shaped proximal recess 298 are also contemplated.

The threaded fastener 290 is positioned through the axial passage 264 defined by the trial component 250, through the axial passage 232 defined by the spacer component 230, and with the threaded end region 292c of the threaded fastener 290 threadedly engaged within the threaded passage portion 216b in the proximal shaft portion 214 of the orthopedic component 210. The head 296 of the threaded fastener 290 is positioned in the counter bore portion 264b of the axial passage 264 in the trial component 250. As should be appreciated, rotation of the threaded fastener 290 (i.e., via application of rotational torque to the head 296) correspondingly threads the threaded end region 292c of the threaded fastener 290 into and along the threaded portion 216b of the passage 216 in the orthopedic component 210, which in turn exerts a compression force by the head 296 against an inner shoulder or ledge 268 defined within the counter bore portion 264b of the axial passage 264. Compression of the head 296 against the inner shoulder or ledge 268 of the trial component 250 displaces the trial component 250 toward and into engagement with the spacer component 230, which in turn compresses the radially-splined surfaces 240, 260 of the spacer component 230 and trial component 250, respectively, into intermeshing engagement with one another. Compression of the radially-splined surfaces 240, 260 into intermeshing engagement selectively prevents further rotation or axial movement of the trial component 250 relative to the spacer component 230 and relative to the orthopedic component 210, thereby locking the trial component 250 in a selected position and orientation relative to the orthopedic component 210.

Referring to FIGS. 10 and 11, in the illustrated embodiment, the spacer component 230 of the trial assembly 220 is keyed to the proximal shaft portion 214 of the orthopedic component 210 to substantially prevent relative rotation therebetween about the longitudinal axis L. Specifically, the spacer component 230 includes an axial projection 244 having an outer surface 246 defining a non-circular outer cross section, and the orthopedic component 210 includes an axial passage 216 defining a distal passage portion 216a with inner surfaces 218 defining a non-circular inner cross section that corresponds to the outer cross section of the axial projection 244. The axial projection 244 of the spacer component 230 is rotationally engaged with the distal passage portion 216a of the orthopedic component 210 to substantially prevent relative rotation between the spacer component 230 and the orthopedic component 210. In the illustrated embodiment, the axial projection 244 and the distal passage portion 216a have a hexagonal-shaped cross section. However, it should be understood and appreciated that other shapes and configurations of the axial projection 244 and the distal passage portion 216a are also contemplated including, for example, a square shape, a double square shape, a rectangular shape, an oblong shape, a splined shape, a Torx shape, a star shape, or any other keyed configuration suitable to rotationally couple the trial spacer 230 with the orthopedic component 210 to substantially prevent relative rotation therebetween about the longitudinal axis L.

As should be appreciated, although the spacer component 230 and the trial component 250 constitute individual pieces, these components are axially coupled, interconnected, or combined with one another to form a single, integrated trial assembly 220, with the spacer component 230 and the trial component 250 being rotationally independent from one another (i.e., the components are free to rotate relative to one another). Additionally, the spacer component 230 and the trial component 250 are axially locked into position atop the proximal shaft portion 214 of the orthopedic component 210 such that the integrated trial assembly 220 functionally operates as if the spacer component 230 and the trial component 250 were provided as separate and independent components.

As should be further appreciated, having the spacer component 230 and the trial component 250 combined into a single, integrated unit simplifies connection or engagement of the trial assembly 220 with the orthopedic component 210. The spacer component 230 is operatively engaged with and axially coupled to the trial component 250 in such a manner as to minimize difficulties in determining when the spacer component 230 is fully seated on the proximal shaft portion 214 of the orthopedic component 210. Further, the trial component 250 is maintained in axial alignment with the spacer component 230. Additionally, compared to traditional/conventional trial systems, the components of the trial assembly 220 (i.e., the trial component 250 and the spacer component 230) are significantly easier to disassemble from the orthopedic component 210, particularly since the integrated trial assembly 220 may be removed as a single unit rather than having to individually remove the trial component 250, and then separately removing the spacer component 230 from the bone passage or canal in view of visual obstructions caused by soft tissue or other surrounding anatomic structures.

In one form of the invention, an orthopedic trial apparatus is provided which includes an orthopedic component and a proximal trial assembly. The orthopedic component has a distal shaft portion configured for positioning within a passage in a bone, and a proximal shaft portion extending from the distal shaft portion. The proximal trial assembly is engaged with the proximal shaft portion of the orthopedic component, and includes a proximal spacer component and a proximal trial component. The proximal spacer component is rotationally engaged with the proximal shaft portion of the orthopedic component to substantially prevent relative rotation therebetween about a longitudinal axis, and the proximal trial component is axially coupled to the proximal spacer component to prevent disengagement of the proximal trial component from the proximal spacer component while permitting selective rotation of the proximal trial component relative to the proximal spacer component about the longitudinal axis.

In another form of the invention, an orthopedic trial apparatus is provided which includes an orthopedic component and a proximal trial assembly. The orthopedic component has a distal shaft portion configured for positioning within a passage in a bone, and a proximal shaft portion extending from the distal shaft portion. The proximal trial assembly is engaged with the proximal shaft portion of the orthopedic component, and includes a proximal spacer component and a proximal trial component. The proximal spacer component is rotationally engaged with the proximal shaft portion of the orthopedic component to substantially prevent relative rotation therebetween about a longitudinal axis, and the proximal trial component is axially aligned with and coupled to the proximal spacer component to prevent axial misalignment and disengagement of the proximal trial component from the proximal spacer component while permitting selective displacement of the proximal trial component relative to the proximal spacer component along the longitudinal axis and selective rotation of the proximal trial component relative to the proximal spacer component about the longitudinal axis.

In a further form of the invention, an orthopedic trial apparatus is provided which includes an orthopedic component and a proximal trial assembly. The orthopedic component has a distal shaft portion configured for positioning within a passage in a bone, and a proximal shaft portion extending from the distal shaft portion. The proximal trial assembly is engaged with the proximal shaft portion of the orthopedic component, and includes a proximal spacer component and a proximal trial component. The proximal spacer component is telescopically engaged with the proximal spacer component to permit selective axial movement therebetween and to maintain axial alignment of the proximal trial component relative to the proximal spacer component generally along the longitudinal axis while permitting selective rotation of the proximal trial component relative to the proximal spacer component about the longitudinal axis. The proximal trial component is axially biased away from the proximal spacer component by a biasing element, and the proximal trial component and the proximal spacer component define anti-rotation elements that are positioned in selective engagement by a locking member to selectively prevent rotation of the proximal trial component relative to the proximal spacer component about the longitudinal axis.

In a further aspect of the invention, the proximal trial component is selectively movable relative to the proximal spacer component in a direction generally along the longitudinal axis.

In a further aspect of the invention, the proximal trial component is axially biased away from the proximal spacer component by a biasing element, and the biasing element may be configured as a spring.

In a further aspect of the invention, the proximal trial component is maintained in axial alignment with the proximal spacer component generally along the longitudinal axis.

In a further aspect of the invention, the proximal trial component is telescopically engaged with the proximal spacer component to permit selective axial movement therebetween and to maintain axial alignment of the proximal trial component relative to the proximal spacer component generally along the longitudinal axis.

In a further aspect of the invention, one of the proximal trial component and the proximal spacer component includes a lateral projection that is axially displaced along an axially-extending groove to permit axial displacement of the proximal trial component relative to the proximal spacer component and to prevent disengagement of the proximal trial component from the proximal spacer component. The lateral projection may be configured as a snap ring positioned within an annular groove defined by one of the proximal trial component and the proximal spacer component, or may be configured as a pin extending laterally from one of the proximal trial component and the proximal spacer component.

In a further aspect of the invention, the proximal trial component and the proximal spacer component define anti-rotation elements that are positioned in selective engagement to selectively prevent rotation of the proximal trial component relative to the proximal spacer component about the longitudinal axis. The anti-rotation elements may be configured as intermeshing radial splines defined on opposing ends of the proximal trial component and the proximal spacer component, and the anti-rotation elements may be selectively engaged with one another by a locking member to selectively prevent rotation of the proximal trial component relative to the proximal spacer component. The locking member may be configured as a locking cap that threadingly engages the proximal shaft portion of the orthopedic component to force the anti-rotation elements into compressing engagement with one another to selectively prevent rotation of the proximal trial component relative to the proximal spacer component. The locking member may also be configured as a threaded fastener extending through the proximal trial component and the proximal spacer component and into threading engagement with the proximal shaft portion of the orthopedic component to force the anti-rotation elements into compressing engagement with one another to selectively prevent rotation of the proximal trial component relative to the proximal spacer component.

In a further aspect of the invention, the proximal spacer component is keyed to the proximal shaft portion of the orthopedic component to substantially prevent relative rotation therebetween about the longitudinal axis. One of the proximal spacer component and the proximal shaft portion may defined a non-circular inner cross section, and another of the proximal spacer component and the proximal shaft portion may define a non-circular outer cross section rotationally engaged with the non-circular inner cross section to substantially prevent relative rotation therebetween.

In a further aspect of the invention, the proximal trial assembly is selectively and removably engaged with the proximal shaft portion of the orthopedic component.

In a further aspect of the invention, the orthopedic component may be configured as a cutting instrument, and the distal shaft portion may be configured as a cutting portion including one or more cutting elements configured to cut bone and at least partially form the passage in the bone.

In a further aspect of the invention, the orthopedic component may be configured as an implant, and the distal shaft portion may be configured as an elongate stem positioned with the passage in the bone. In one form, the implant may be configured as a hip prosthesis, and with elongate stem defining a modular stem portion configured for engagement with a modular head portion.

Various changes and modifications to the described embodiments described herein will be apparent to those skilled in the art, and such changes and modifications can be made without departing from the spirit and scope of the invention and without diminishing its intended advantages. Additionally, while the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

The invention claimed is:

1. An orthopedic trial apparatus, comprising:
an orthopedic component having a distal shaft portion configured for positioning within a passage in a bone, and a proximal shaft portion extending from the distal shaft portion; and
a proximal trial assembly engaged with the proximal shaft portion of the orthopedic component, the proximal trial assembly including:
a proximal spacer component rotationally engaged with the proximal shaft portion of the orthopedic component to substantially prevent relative rotation therebetween about a longitudinal axis; and
a proximal trial component axially coupled to the proximal spacer component to prevent disengagement of the proximal trial component from the proximal spacer component while permitting selective rotation of the proximal trial component relative to the proximal spacer component about the longitudinal axis;
wherein one of the proximal trial component and the proximal spacer component comprises a lateral projection comprising a snap ring positioned within and axially displaceable along an axially-extending annular groove formed in the other one of the proximal trial component and the proximal spacer component to permit axial displacement of the proximal trial component relative to the proximal spacer component and to prevent disengagement of the proximal trial component from the proximal spacer component.

2. The orthopedic trial apparatus of claim 1, wherein the proximal trial component is selectively movable relative to the proximal spacer component in a direction generally along the longitudinal axis.

3. The orthopedic trial apparatus of claim 2, wherein the proximal trial component is axially biased away from the proximal spacer component by a biasing element.

4. The orthopedic trial apparatus of claim 3, wherein the biasing element comprises a spring.

5. The orthopedic trial apparatus of claim 1, wherein the proximal trial component is maintained in axial alignment with the proximal spacer component generally along the longitudinal axis.

6. The orthopedic trial apparatus of claim 1, wherein the proximal trial component is telescopically engaged with the proximal spacer component to permit selective axial movement therebetween and to maintain axial alignment of the proximal trial component relative to the proximal spacer component generally along the longitudinal axis.

7. The orthopedic trial apparatus of claim 1, wherein the proximal trial component and the proximal spacer component define anti-rotation elements that are positioned in selective engagement to selectively prevent rotation of the proximal trial component relative to the proximal spacer component about the longitudinal axis.

8. The orthopedic trial apparatus of claim 7, wherein the anti-rotation elements comprise intermeshing radial splines defined on opposing ends of the proximal trial component and the proximal spacer component.

9. The orthopedic trial apparatus of claim 7, wherein the anti-rotation elements are selectively engaged with one another by a locking member to selectively prevent rotation of the proximal trial component relative to the proximal spacer component.

10. The orthopedic trial apparatus of claim 9, wherein the locking member comprises a locking cap that threadingly engages the proximal shaft portion of the orthopedic component to force the anti-rotation elements into compressing engagement with one another to selectively prevent rotation of the proximal trial component relative to the proximal spacer component.

11. The orthopedic trial apparatus of claim 1, wherein the proximal spacer component is keyed to the proximal shaft portion of the orthopedic component to substantially prevent relative rotation therebetween about the longitudinal axis.

12. The orthopedic trial apparatus of claim 11, wherein one of the proximal spacer component and the proximal shaft portion comprises a non-circular inner cross section, and another of the proximal spacer component and the proximal shaft portion comprises a non-circular outer cross section rotationally engaged with the non-circular inner cross section to substantially prevent relative rotation therebetween.

13. The orthopedic trial apparatus of claim 1, wherein the proximal trial assembly is selectively and removably engaged with the proximal shaft portion of the orthopedic component.

14. The orthopedic trial apparatus of claim 1, wherein the orthopedic component comprises a cutting instrument, and wherein the distal shaft portion comprises a cutting portion including one or more cutting elements configured to cut bone and at least partially form the passage in the bone.

15. The orthopedic trial apparatus of claim 1, wherein the orthopedic component comprises an orthopedic implant, and wherein the distal shaft portion comprises an elongate stem positionable within the passage in the bone.

16. The orthopedic trial apparatus of claim 15, wherein the implant comprises a hip prosthesis, and wherein the elongate stem comprises a modular stem portion configured for engagement with a modular head portion.

17. An orthopedic trial apparatus, comprising:
an orthopedic component having a distal shaft portion configured for positioning within a passage in a bone, and a proximal shaft portion extending from the distal shaft portion; and
a proximal trial assembly engaged with the proximal shaft portion of the orthopedic component, the proximal trial assembly including:
  a proximal spacer component rotationally engaged with the proximal shaft portion of the orthopedic component to substantially prevent relative rotation therebetween about a longitudinal axis;
  a proximal trial component axially aligned with and coupled to the proximal spacer component to prevent axial misalignment and disengagement of the proximal trial component from the proximal spacer component while permitting selective displacement of the proximal trial component relative to the proximal spacer component along the longitudinal axis and selective rotation of the proximal trial component relative to the proximal spacer component about the longitudinal axis; and
  a snap ring positioned within and axially displaceable in an axially-extending annular groove formed in the proximal spacer component to permit axial displacement of the proximal trial component relative to the proximal spacer component and to prevent disengagement of the proximal trial component from the proximal spacer component.

18. The orthopedic trial apparatus of claim 17, wherein the proximal trial component is axially biased away from the proximal spacer component by a biasing element.

19. The orthopedic trial apparatus of claim 17, wherein the proximal trial component is telescopically engaged with the proximal spacer component to permit selective axial movement therebetween and to maintain axial alignment of the proximal trial component relative to the proximal spacer component generally along the longitudinal axis.

20. The orthopedic trial apparatus of claim 17, wherein the proximal trial component and the proximal spacer component define anti-rotation elements that are positioned in selective engagement by a locking member to selectively prevent rotation of the proximal trial component relative to the proximal spacer component about the longitudinal axis.

21. An orthopedic trial apparatus, comprising:
an orthopedic component having a distal shaft portion configured for positioning within a passage in a bone, and a proximal shaft portion extending from the distal shaft portion; and
a proximal trial assembly engaged with the proximal shaft portion of the orthopedic component, the proximal trial assembly including:
  a proximal spacer component rotationally engaged with the proximal shaft portion of the orthopedic component to substantially prevent relative rotation therebetween about a longitudinal axis; and
  a proximal trial component telescopically engaged with the proximal spacer component to permit selective axial movement therebetween and to maintain axial alignment of the proximal trial component relative to the proximal spacer component generally along the longitudinal axis while permitting selective rotation of the proximal trial component relative to the proximal spacer component about the longitudinal axis;
wherein the proximal trial component is axially biased away from the proximal spacer component by a biasing element;

wherein the proximal trial component and the proximal spacer component define anti-rotation elements that are positioned in selective engagement by a locking member to selectively prevent rotation of the proximal trial component relative to the proximal spacer component about the longitudinal axis; and wherein one of the proximal trial component and the proximal spacer component includes a snap ring positioned within and axially displaceable along an axially-extending annular groove formed in the other one of the proximal trial component and the proximal spacer component to permit axial displacement of the proximal trial component relative to the proximal spacer component and to prevent disengagement of the proximal trial component from the proximal spacer component.

* * * * *